US00PP10772P

United States Patent [19]

Geers

[11] Patent Number: Plant 10,772

[45] Date of Patent: Feb. 2, 1999

[54] WEIGELA PLANT NAMED 'ALEXANDRA'

[75] Inventor: Herman Geers, Boskoop, Netherlands

[73] Assignee: Spring Meadow Nursery, Inc., Grand Haven, Mich.

[21] Appl. No.: 923,731

[22] Filed: Sep. 4, 1997

[51] Int. Cl.[6] ..... A01H 5/00

[52] U.S. Cl. ..... Plt./54.1

[58] Field of Search ..... Plt./54.1

[56] References Cited

U.S. PATENT DOCUMENTS

P.P. 492 11/1941 Cumming ..... Plt./54.1

P.P. 5,555 9/1985 Geers, Jr. ..... Plt./54.1

P.P. 8,348 8/1993 Weigle ..... Plt./54.1

*Primary Examiner*—Howard J. Locker

*Assistant Examiner*—Kent L. Bell

*Attorney, Agent, or Firm*—C. A. Whealy

[57] ABSTRACT

A distinct cultivar of Weigela plant named 'Alexandra', characterized by its erect growth habit that eventually becomes spreading and arching; large dark reddish brown leaves with contrasting bright green midveins; leaf color that darkens during the summer; large and long-lasting dark pink flowers that become dark red with subsequent development; and moderate to rapid growth rate.

2 Drawing Sheets

The present invention relates to a new and distinct cultivar of Weigela plant, botanically known as *Weigela florida,* and hereinafter referred to by the cultivar name 'Alexandra'.

The new cultivar is a product of a planned breeding program conducted by the inventor in Boskoop, The Netherlands. The objective of the breeding program was to develop new Weigelas with dark leaves and attractive flower colors. The new cultivar originated from a cross made by the inventor of the nonpatented *Weigela florida* cultivar 'Victoria' as the female or seed parent with the proprietary *Weigela florida* seedling number 21 as the male or pollen parent. The cultivar 'Alexandra' was discovered and selected by the inventor as a flowering plant within the progeny of the stated cross in a controlled environment in Boskoop, The Netherlands.

Asexual reproduction of the new cultivar by cuttings taken at Boskoop, The Netherlands, and Grand Haven, Mich., has shown that the unique features of this new Weigela plant are stable and reproduced true to type in successive generations of asexual reproduction.

The following traits have been repeatedly observed and are determined to be the unique characteristics of 'Alexandra'. These characteristics in combination distinguish 'Alexandra' as a new and distinct cultivar:

1. Erect growth habit eventually becoming spreading and arching.

2. Large dark reddish brown leaves with contrasting bright green midveins. Leaf color darkens during the summer.

3. Large and long-lasting dark pink flowers that become dark red with subsequent development.

4. Moderate to rapid growth rate.

In side-by-side comparisons in Grand Haven, Mich., under commercial practice, plants of the new Weigela differed from plants of the parent cultivar 'Victoria' in the following characteristics:

1. Plants of the new Weigela are more upright and broader than plants of the cultivar 'Victoria'.

2. Plants of the new Weigela have longer leaves than plants of the cultivar 'Victoria'.

3. Leaves of plants of the new Weigela are glossier and have a more intense reddish color than leaves of plants of the cultivar 'Victoria'. During the summer, reddish leaf color darkens on plants of the new Weigela whereas leaf color fades during the summer on plants of the cultivar 'Victoria'.

4. Midveins of leaves of plants of the new Weigela are lighter and brighter green than midveins of leaves of plants of the cultivar 'Victoria'.

5. Plants of the new Weigela have longer and lighter green petioles than plants of the cultivar 'Victoria'.

6. Plants of the new Weigela have longer internodes than plants of the cultivar 'Victoria'.

7. Flowers of plants of the new Weigela are larger, longer-lasting, and darker pink than flowers of plants of the cultivar 'Victoria'.

8. Flower throat of plants of the new Weigela do not display the prominent yellow throat color of plants of the cultivar 'Victoria'.

9. Plants of the new Weigela have longer sepals than plants of the cultivar 'Victoria'. Additionally, sepals are dark red on plants of the new Weigela whereas sepals are brownish on plants of the cultivar 'Victoria'.

10. Plants of the new Weigela have longer, more flexible, and redder peduncles than plants of the cultivar 'Victoria'.

In side-by-side comparisons in Grand Haven, Mich., under commercial practice, plants of the new Weigela differed from plants of the nonpatented *Weigela florida* Nana purpurea variety 'Java Red' in the following characteristics:

1. Plants of the new Weigela are much larger than plants of the variety 'Java Red'.

2. Plants of the new Weigela have longer and smoother leaves than plants of the variety 'Java Red'.

3. Leaves of plants of the new Weigela are a more intense reddish color than leaves of plants of the variety 'Java Red'. During the summer, reddish leaf color darkens on plants of the new Weigela whereas leaf color fades during the summer on plants of the variety 'Java Red'.

4. Midveins of leaves of plants of the new Weigela are lighter and brighter green than midveins of leaves of plants of the variety 'Java Red'.

5. Plants of the new Weigela have longer and lighter green petioles than plants of the variety 'Java Red'.

6. Plants of the new Weigela have longer internodes than plants of the variety 'Java Red'.

7. Flowers of plants of the new Weigela are larger, longer-lasting, and darker pink than flowers of plants of the variety 'Java Red'.

8. Flower throat of plants of the new Weigela do not display the prominent yellow throat color of plants of the variety 'Java Red'.

9. Plants of the new Weigela have longer sepals than plants of the variety 'Java Red'. Additionally, sepals are dark red on plants of the new Weigela whereas sepals are brownish on plants of the variety 'Java Red'.

10. Plants of the new Weigela have longer and more flexible peduncles than plants of the variety 'Java Red'.

The cultivar 'Alexandra' has not been observed under all possible environmental conditions. The phenotype may vary somewhat with variations in environment such as temperature and light intensity, without, however, any variance in genotype.

BRIEF DESCRIPTION OF THE PHOTOGRAPHS

The accompanying colored photographs illustrate the overall appearance of the new Weigela, showing the colors as true as it is reasonably possible to obtain in colored reproductions of this type.

The first photograph comprises a close-up view of typical flowers and leaves of the cultivar 'Alexandra'.

The second photograph comprises a close-up view of typical leaves of the cultivar 'Alexandra'. Flower and foliage colors in the photographs may appear different than the actual colors due to light reflectance.

DETAILED BOTANICAL DESCRIPTION

The following observations, measurements and comparisons describe plants grown in Grand Haven, Mich., under production conditions. Color references are made to The Royal Horticultural Society Colour Chart except where general terms of ordinary dictionary significance are used.

Botanical classification: *Weigela florida* cultivar 'Alexandra'.

Parentage:

*Female or seed parent.*—*Weigela florida* cv. 'Victoria' (not patented).

*Male or pollen parent.*—Inventor's proprietary seedling of *Weigela florida,* code number 21.

Propagation:

*Type cutting.*—Cuttings.

*Time to initiate roots.*—About 20 days at 17° to 20° C.

*Rooting habit.*—Fine and fibrous.

Plant description:

*Form.*—Perennial shrub; dense and rounded; initially upright and eventually becoming spreading and arching.

*Branching habit.*—Basally branching, pruning increases branching.

*Plant size.*—Height: 1.25 to 1.5 meters from soil level to top of plant plane during a growing season. Diameter or area of spread: About 2 meters. Suitable containers: 1 to 3-gallon.

*Vigor/growth rate.*—Moderate to fast.

*Crop time.*—About one year from a rooted cutting to a finished 1-gallon container.

*Stem description.*—Internode length: 5 to 8 cm. Color: Mature, 201A to 201D. Texture: Pubescent, lenticels present.

*Foliage description.*—Leaves single and generally symmetrical, opposite arrangement. Very durable, resistant to stress. Size: Length: 5 to 9 cm. Width: 2.5 to 5 cm. Shape: Elliptic to ovate/oblong. Apex: Acuminate to acute. Base: Cuneate/rounded to acute. Margin: Serrulate. Texture: Smooth, slight to high gloss. Color: Leaf color darkens during periods of high light and/or high temperatures. Young leaves: Upper surface: Between 202A and 187A. Lower surface: 187A. Fully expanded leaves: Upper surface: 187A. Lower surface: 187B. Venation: Upper surface: 141D. Lower surface: 142C. Petiole: Length: 8 to 10 mm. Diameter: 1 to 1.5 mm. Color: 141D.

Flower description:

*Flower type and habit.*—Single or typically arranged in cymes with 2 to 8 flowers each; funnelform/campanulate flowers; five-petaled, fused and slightly overlapping; terminal or axillary; persistent. Flowers typically last 4 to 8 weeks. Numerous flowers per plant.

*Natural flowering season.*—Plants flower during May/June in the Northern Hemisphere; plants will reflower if pruned.

*Fragrance.*—None.

*Flower bud.*—Length: 4 to 5.5 cm. Diameter: 1.0 to 1.2 cm. Shape: Funnelform. Color: 59A to 60B.

*Flower size.*—Diameter: 2 to 2.5 cm. Height: 4 to 5 cm.

*Petals.*—Length: 0.5 to 1 cm. Width: About 1 cm. Shape: Reniform, rounded. Apex: Rounded. Margin: Slightly undulate, entire. Color: When opening: Upper surface: 66C. Lower surface: 61A. Fully opened: Upper surface: 66C to 66D, with subsequent development, flower color darkens to 61A. Lower surface: 60D.

*Sepals.*—Quantity: Five. Length: 8 to 12 mm. Calyx diameter: 1 to 2 cm. Shape: Linear/lanceolate. Apex: Acuminate. Margin: Entire/serrulate. Color: 59A.

*Peduncle.*—Length: 2 to 2.5 cm. Strength: Flexible. Color: 59A.

*Reproductive organs.*—Stamens: Stamen number: Five. Anther size: About 5 mm. Anther and pollen color: 160D. Filament color: 61C. Pistils: Pistil length: 4 to 5.5 cm. Style length: 3.75 to 5 cm. Stigma color: 160D. Style color: 186C. Seed Production: Seeds typical of the species.

Disease resistance: Plants of the new Weigela are not susceptible to diseases common to Weigela. Hardiness: Rated hardy to USDA Hardiness Zone 4 to 8.

It is claimed:

1. A new and distinct cultivar of Weigela plant named 'Alexandra', as illustrated and described.

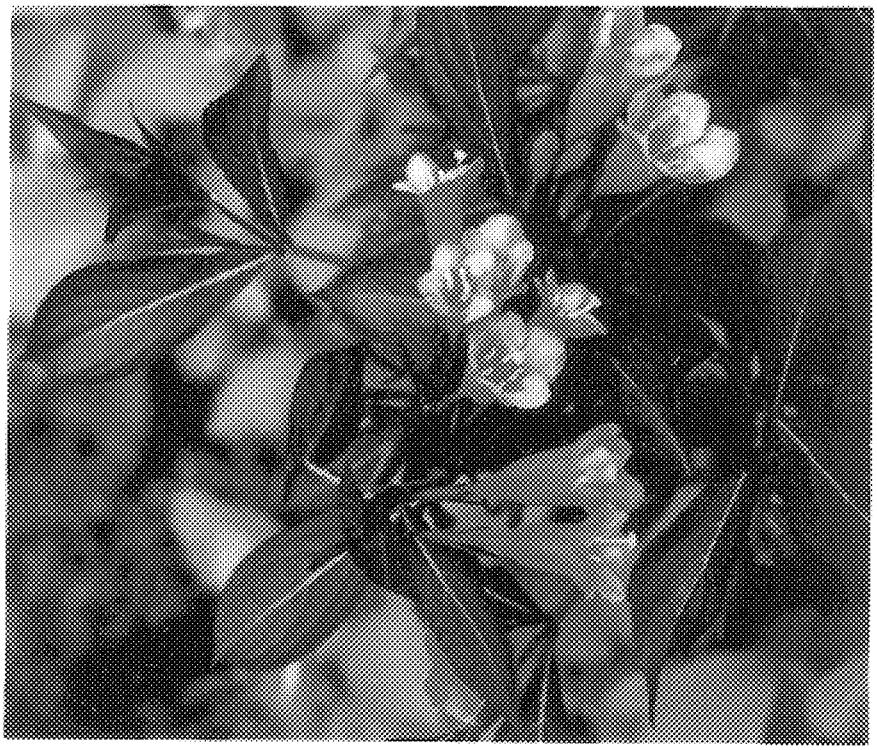

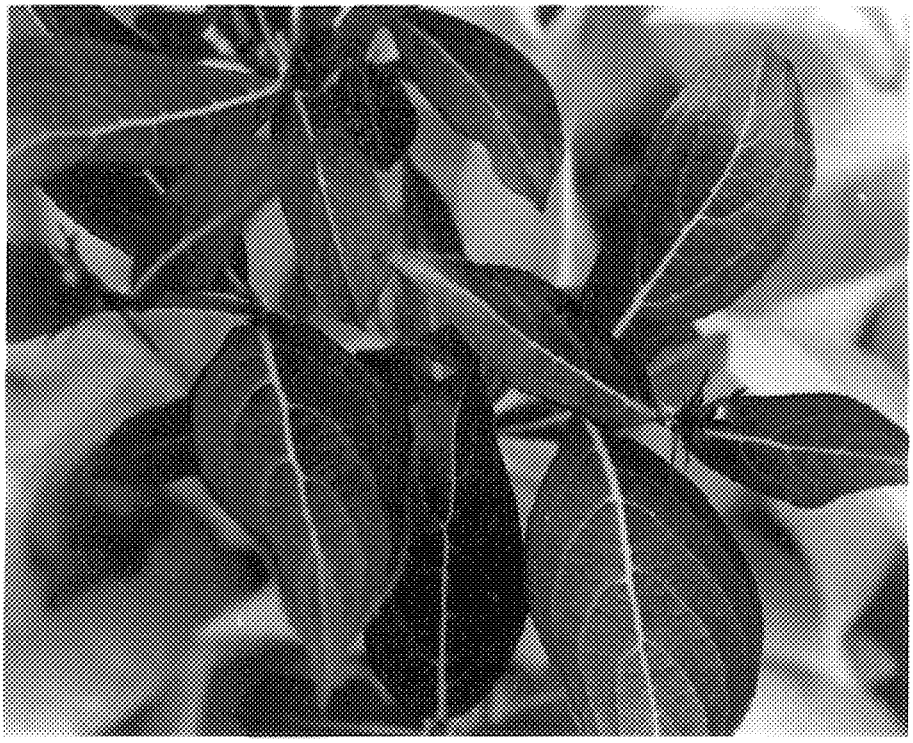

* * * * *